United States Patent
Boccella et al.

(10) Patent No.: US 12,366,547 B2
(45) Date of Patent: Jul. 22, 2025

(54) POLYMER MATRIX ELECTRODES (71) Applicant: TECNOSENS S.R.L., Rome (IT)

(72) Inventors: Antonio Boccella, Rome (IT); Manlio Valentini, Rome (IT)

(73) Assignee: TECNOSENS S.R.L., Rome (IT)

( * ) Notice: Subject to any disclaimer, the term of this patent is extended or adjusted under 35 U.S.C. 154(b) by 627 days.

(21) Appl. No.: 17/624,859

(22) PCT Filed: Jul. 3, 2020

(86) PCT No.: PCT/EP2020/068862
§ 371 (c)(1),
(2) Date: Jan. 5, 2022

(87) PCT Pub. No.: WO2021/004956
PCT Pub. Date: Jan. 14, 2021

(65) Prior Publication Data
US 2022/0252537 A1 Aug. 11, 2022

(30) Foreign Application Priority Data
Jul. 5, 2019 (IT) .................. 102019000011004

(51) Int. Cl.
C08K 3/08 (2006.01)
C08F 114/22 (2006.01)
C08K 3/04 (2006.01)
G01N 27/30 (2006.01)
G01N 27/416 (2006.01)
G01N 33/18 (2006.01)

(52) U.S. Cl.
CPC .......... *G01N 27/308* (2013.01); *C08F 114/22* (2013.01); *C08K 3/041* (2017.05); *C08K 3/08* (2013.01); *G01N 27/30* (2013.01); *G01N 27/301* (2013.01); *G01N 27/4166* (2013.01); *G01N 33/1886* (2013.01); *C08K 2003/0806* (2013.01); *C08K 2003/0831* (2013.01)

(58) Field of Classification Search
CPC .. G01N 27/308; G01N 27/30; G01N 27/4166; G01N 33/1886; G01N 33/182; G01N 27/4168; G01N 27/416; C08F 114/22; C08K 3/041; C08K 2003/0806; C08K 2003/0831
USPC ....................................... 264/104
See application file for complete search history.

(56) References Cited

U.S. PATENT DOCUMENTS

| 6,315,956 B1 | 11/2001 | Foulger |
| 2005/0036020 A1 | 2/2005 | Li et al. |
| 2007/0023283 A1 | 2/2007 | Huang |
| 2012/0068759 A1* | 3/2012 | Clark .................. A61B 5/1036 327/517 |
| 2012/0181173 A1 | 7/2012 | Ochoteco et al. |
| 2012/0277353 A1 | 11/2012 | Mulholland |
| 2015/0276644 A1 | 10/2015 | Striemer |

FOREIGN PATENT DOCUMENTS

| CN | 105669972 A | 6/2016 |
| EP | 2336765 A1 | 6/2011 |
| EP | 3037811 A1 | 6/2016 |
| TW | 201211172 A | 3/2012 |
| WO | 2005062405 A2 | 7/2005 |

OTHER PUBLICATIONS

Office Action issued Apr. 1, 2024 in connection with counterpart Chinese Patent Application No. 202080059876.7.
Anonymous "Flame retardant, specials, high performance thermoplastics, compounds—Lati Material Database", Jan. 1, 2018, p. 1, retrieved from the internet: URL: https://lambda.lati.com/index.aspx.
Ensinger Group: "Tecapeek ELS nano black—stock shapes (rods, plates, tubes)", In "Tecapeek ELS nano black—stock Shapes (rods, plates, tubes)", Feb. 20, 2018, Ensinger Group, p. 1.
Quan H et al, "Electrochemical oxidation of glucose on silver nanoparticle-modified composite electrodes", Electrochimica Acta, Elsevier Amsterdam, NL, vol. 55, No. 7, Feb. 28, 2010, pp. 2232-2237.
Search Report and Written Opinion of PCT/EP2020/068862 of Sep. 25, 2020.
Letter reporting office action issued Nov. 25, 2024 in connection with counterpart Chinese Patent Application No. 202080059876.7, including English translation of the Office Action issued issued Nov. 25, 2024 in connection with counterpart Chinese Patent Application No. 202080059876.7.
Office Action issued Nov. 25, 2024 in Chinese Language related to patent application No. 202080059876.7.
Letter of foreign associate reporting Chinese Office Action and Office Action issued Apr. 30, 2025 in counterpart Chinese application No. 202080059876.7.

* cited by examiner

Primary Examiner — Hannah J Pak
(74) Attorney, Agent, or Firm — Silvia Salvadori, P.C.; Silvia Salvadori (57) ABSTRACT

Electrochemical probes (or sensors), resistant to corrosive agents present in seawaters or in industrial waters, useful for detecting compounds present in water, are here described, wherein said probes comprise at least one polymer matrix electrode, in which said electrode is selected from the group comprising counter electrode, reference electrode and working electrode.

3 Claims, 3 Drawing Sheets

POLYMER MATRIX ELECTRODES

This application is a U.S. national stage of PCT/EP2020/068862 filed on 3 Jul. 2020, which claims priority to and the benefit of Italian Application No. 102019000011004 filed on 5 Jul. 2019 the contents of which are all incorporated herein by reference in their entireties.

FIELD OF THE INVENTION

The present invention relates to new electrochemical probes (or sensors), resistant to corrosive agents present in seawaters or in industrial waters, useful for detecting compounds present in water, wherein said probes comprise at least one polymer matrix electrode, in which said electrode is selected from the group comprising counter electrode, reference electrode and working electrode.

In other words, the present invention relates to the use of polymeric materials for preparing electrodes for electrochemical probes; in which said electrodes are cheap, versatile and resistant to corrosive agents present in seawaters or in waters of industrial origin; as well as a method for their preparation.

According to an embodiment, the present invention relates to conventional electrochemical probes known in the art wherein at least one electrode is a polymer matrix electrode.

BACKGROUND OF THE INVENTION

The specific electrical conductance of a conductor defines the electrical conductivity "a". The instrument used to measure electrical conductivity is called "conductivity meter". According to the International System its unit of measurement is "Siemens/meter" (S/m).

The electrochemical probes belong to the field of amperometric sensors, they are used for measuring the concentration of chemical agents present, for example, in seawaters, swimming pools or industrial waters or for measuring other water parameters.

By the term "amperometry" is meant a specific voltametric technique in which the electric current is measured at a fixed potential selected to obtain the discharge of the electroactive species on the surface of the working electrode.

The curve obtained is a plot of the electric current as a function of the time and the correlation between the current and the analyte concentration is ruled by the Cottrell equation and is well known to the skilled in the art.

In amperometry the typical instrumentation used comprises an auxiliary electrode, a reference electrode, in which the potential must be known and constant over time and independent from the composition of the solution containing the analyte, in which said reference electrode is immersed, a working electrode, the response of which depends on the concentration of the analyte and, finally, a device useful for applying the potential and recording the electric current produced by the species of interest during the oxidation or reduction reaction on the surface of the working electrode.

Corrosion is the physical-chemical interaction between a metal and its environment resulting in alterations in the properties of the metal and which can compromise the functionality of the metal or of the technical plant of which it is part (see ISO 8044:2010).

The undesired outcomes of corrosion can span from an external defect to the complete failure of technical systems with considerable economic damage and even dangers for people.

With the metals commonly used in engineering, such as carbon steel, stainless steel, zinc, copper and aluminium, the typical corrosion process can be considered as the reverse of the thermodynamically favoured reaction of the metal extraction process.

Like all chemical reactions, the corrosive processes occur when the environmental conditions are favourable.

Different Types of Corrosion can Occur:
- corrosion due to chemical reaction: it occurs at high temperatures, when the metal reacts to hot gases and forms an oxide layer;
- corrosion by metal-physical reaction: it causes embrittlement due to hydrogen that diffuses into a metal, with the potential failure of a component;
- electrochemical corrosion: it involves an electrical exchange by means of electrons in the metal and the ions in a conductive electrolyte, such as a water film on the metal surface;
- uniform corrosion, or surface corrosion: it is a form of corrosion, in which the surface is almost uniformly removed.

The corrosion rate is usually indicated in micrometers per year ($\mu m/y$).

Using average values it is possible to calculate the life expectancy of a component and thus enhance it by increasing its thickness.

Uniform corrosion occurs, for example, in carbon steel and galvanized steel under exposure conditions (https://www.hilti.it/content/dam/documents/pdf/e4/engineering/manuals/Hilti_Corrosion-Handbook_W4412_it.pdf).

The polymeric materials, also called plastic materials or synthetic resins, are substances formed by very large organic molecules, macromolecules, deriving from the union, by chemical bonds, of small units called monomers.

These units may be of one or more species. Some polymers such as cellulose, natural rubber, resins are of natural origin; most of the polymers known to date are of artificial origin. The first industrial polymers (celluloid and Bakelite) were produced in 1870 and 1907 respectively.

The polymeric materials are characterized by low specific weight, by considerable chemical inertia, in many cases by low yield strength and by great elongation at break. They have a low resistance to high temperatures as a limit for applications.

When considering their structure, the polymeric materials are distinguished in linear polymers, if the monomeric units are bound to form long chains, more or less entangled; in branched polymers, when lateral branches depart from a main chain and in crosslinked polymers, when some branches chemically connect more chains.

The polymers can also be classified, because of their behaviour as temperature varies, in thermoplastics and in thermosetting materials.

Thermoplastic polymers are polymers formed by linear chains that soften when heated and recover their solid consistency at lower temperature, according to a cycle that can be repeated countless times.

To this group belong, for example, polyethylene or polythene (PE); polypropylene (PP); polystyrene (PS); polymethylmethacrylate (PMMA); polyvinylchloride (PVC); polyacrylonitrile-butadiene-styrene (ABS); polyacrylonitrile (PAN); polyethyleneterephthalate (PET); polyamides (PA); polycarbonate (PC); polybutylene terephthalate (PBT); and polytetrafluoroethylene (PTFE).

The thermosetting polymers are polymers formed by large crosslinked molecules that, when heated, first soften and then definitively consolidate blocking the flowing.

To this group, belong, for example, saturated and unsaturated polyester; epoxy, urea/formaldehyde, melamine/formaldehyde and phenolic/formaldehyde polymers.

Among the polymeric resins there are polyacrylic resins; polyvinyl; fluorinated; polyamide; acetal; polyacetal; polyoxymethylene acetal; polyphenylene oxidics; cellulosic; polyester; epoxy; polyurethane; amine, polyvinylidene fluoride or polyvinylidene fluoride.

Silicone materials belong to the non-conductive polymers (see http://corsiadistanza.polito.it/on-line/Materiali/pdf/dispensa_materiali.pdf).

The electrical conductors are materials capable of flowing electric current through them. The most known metal electrical conductors are silver, silver nanowires; copper; gold; aluminium; zinc; chromium; tin; iridium; tungsten; nickel; iron; platinum; lead.

The most known non-metallic electrical conductors are carbon and its derivatives such as graphene or carbon nanotubes. Ceramic conductors such as indium-tin oxide (ITO) or zinc aluminium oxide (AZO) also belong to the conductive materials.

In recent years, numerous efforts have been made in the field of research to find viable alternatives for metal substitution, traditionally used for many types of electrical products and components.

The need to replace metals with alternative materials is due to their high weight, to their production processes, often expensive and limiting in the forms obtainable, and sometimes also to corrosion problems often requiring recourse to protective surface coatings, which are expensive and polluting.

Often the reason why a component is made by metal is not linked to its mechanical characteristics, but to its high thermal and electrical conductivity properties.

Polymers, commonly known as insulating materials, therefore previously discarded, have now become an interesting starting material to industrially prepare, or find on the market, conductive or non conductive polymers or polymeric resins, because they can be enriched with metallic or non-metallic electrical conductors (http://www.matech.it/downloads/websiteMat/news/417/Conducibilit % C3% A0.pdf).

To date on the market many devices are available suitable for the measure of some analytes concentration of analytes or other parameters in samples of marine waters, pools or industrial water, by using, for example, a colorimetric or electrochemical detection.

In *Analytica Chimica Acta* (2005), 537:293-298 platinum, gold and glassy carbon electrodes are described. These types of electrodes have the disadvantage of undergoing a passivation process of the electrode surface in the presence of high concentrations of free chlorine.

In https://www.prominent.it/it/Prodotti/Prodotti/Sistemi-di-misura-e-regolazione-sensori/Sensori/p-sensors-free-chlorine.html many probes and/or electrodes for measuring pH or electrolytes dissolved in water are described.

In https://www.ensingerplastics.com/it-it/semilavorati/prodotti-semilavorati/peek-conduttivo-tecapeek-els-cf30-black an electrically conductive polymer material reinforced with carbon fibres (Tecapeek ELS CF30, Black®) is described.

In https://www.ensingerplastics.com/it-it/semilavorati/prodotti-semilavorati/peek-tecapeek-els-nano-black an electrically conductive polymer material reinforced with carbon nanotubes (Tecapeek ELS nano Black®) is described.

On the market there are many companies, which offer electrochemical sensors or electrochemical probes for pH measurement of the concentration of compounds dissolved in water, but none of them offer an electrochemical sensor or an electrochemical probe comprising an auxiliary electrode, a reference electrode and/or a working electrode prepared with one or more conductive polymeric materials.

As above mentioned, the electrochemical probes on the market contain counter electrodes, reference electrodes and working electrodes made of conductive metal, such as steel, gold, silver, platinum, nickel. The best free chlorine probes that are commercially available have a steel counter electrode, a silver reference electrode and a gold working electrode (sonda per Cloro libero, organico ed inorganico Tecnosens, modello NCL T20 e NCL T2 http://www.t-sens.eu).

Steel electrodes oxidize easily and must be replaced frequently, otherwise the measure would be altered.

This implies high maintenance costs of the probe or (very often) the replacement of an entire damaged electrochemical probe with a new probe, in which, in addition to the new steel electrode, a new silver reference electrode and a new gold working electrode are also present.

Usually working and reference electrodes are immersed in an electrolytic solution which protects them and allows their operation. These electrodes come into contact with the water to be analysed by means of a membrane and therefore do not oxidize/degrade in short times, but have very high production costs.

The production costs are linked both to the cost of the raw material used, gold or silver, and to the cost of the process for preparing electrodes made of precious metals.

In fact, the processing of gold and silver for obvious reasons must be carried out in controlled environments, where it is possible to recover all the waste materials which have very high commercial values.

It is well known to the skilled in the art that the costs of managing the electronic/sensor system in "water control" environment have significantly high costs.

It is also evident to the expert in the art that to have available:
  new counter-electrodes which do not have the disadvantages of the steel electrodes mentioned above;
  new reference and working electrodes obtained using materials much less expensive than silver or gold; and/or
  new methods of preparing these three electrodes which are simpler and therefore less expensive;
  is a perceived need in the art.

DESCRIPTION OF THE INVENTION

The present invention relates to new electrochemical sensors and electrochemical probes, useful for the determination of compounds dissolved in water, which are significantly more resistant to corrosive agents present in sea water or industrial waters, significantly less expensive both in the materials in which they are made and in the methods for their preparation,
  wherein said probes comprise at least one auxiliary electrode (hereinafter also identified as counter electrode) and/or at least one reference electrode and/or at least one working electrode; wherein said electrodes are obtained (made) using a polymeric matrix comprising at least one conductive polymer, or at least one non-conductive or poorly conductive polymer in combination/integrated with at least one conductive metallic or non-metallic material.

According to the present invention, the term:
"electrochemical sensor" (or electrochemical probe) refers to a sensor (or probe) comprising at least one auxiliary electrode and/or at least one reference electrode and/or at least one working electrode;
electrochemical sensor or electrochemical probe will not refer to electrochemical sensors, electrodes or probes printed on paper or on a polymeric "surface/support";
conductive polymer will refer to a polymer able to provide an amount of electricity sufficient to "operate" a counter electrode, a reference electrode or a working electrode (good electrically conductive polymer);
"non-conductive or poorly conductive" polymer will refer to a polymer not suitable to provide an amount of electricity sufficient to "operate" a counter electrode, a reference electrode or a working electrode (prior to use it must be suitably integrated/placed in combination with a conductive metallic or non-metallic material);
"conductive metallic or non-metallic" material will refer to an electric conductor (metallic and/or non-metallic) selected for a non-limiting example from carbon; carbon nanotubes; carbon nanohorns; carbon black; graphite, graphene, carbon fullerenes; silver; copper; gold; aluminium; zinc; chromium; tin; iridium; tungsten; nickel; iron; platinum; lead; indium-tin oxide; aluminium-tin oxide.

According to the present invention, the term "polymer matrix" refers to:
at least one conductive polymer, at least one conductive resin or mixtures thereof;
at least one non-conductive or poorly conductive polymer in admixture with at least one conductive polymer;
at least one non-conductive or poorly conductive resin in admixture with at least one conductive resin;
at least one non-conductive or poorly conductive polymer in admixture with at least one conductive resin;
at least one non-conductive or poorly conductive resin in admixture with at least one conductive polymer;
at least one non-conductive or poorly conductive polymer in combination with at least one conductive metallic or non-metallic material;
at least one non-conductive or poorly conductive resin in combination with at least one conductive metallic or non-metallic material;
at least one non-conductive or poorly conductive polymer in admixture with at least one non-conductive or poorly conductive resin in combination with at least one conductive metallic or non-metallic material; or
to a "suitable material", i.e. ready to be used to make the new electrode according to the invention.

According to the present invention, the term "suitable material", i.e., ready to be used to construct the new electrode according to the invention means the material obtained, for example, at the end of the preparation method according to the invention, which follows.

It is therefore an object of the present invention a method for the preparation of a "polymeric matrix" electrode comprising the following steps:
First Step:
a "polymer" is provided selected from the group comprising: ethyl acrylate polymer, acrylonitrile-butadiene or styrene butadiene copolymer, cellulose, epoxy resin, ethylene acrylic acid copolymer, fluoropolymer, natural rubber, melamine formaldehyde or melamine resin, hydrogenated nitrile rubber, polyethylene oxide or PEG, poly(4-methyl-1-pentene), polybutylene, polyacetal, polyacetylene, polyacrylic acid, polyacrylonitrile, polyamide 6, polyamide, polyaniline, polybenzimidazole, polybutadiene, polybutylene terephthalate, polycarbonate, polychloroprene, polydimethylsiloxane (silicones), polyepichlorohydrin, natured and unsaturated polyester, polyetherketone, polyetherimide, polyethylene, low-density polyethylene, chlorosulfonated polyethylene, high-density polyethylene, poly(3,4-ethylenedioxythiophene), polyethylene terephthalate, polyphenylene sulfide, poly(phenylene oxide), polyphenylsulfone, polyisoprene, polyisothianaphene, phenolic/formaldehyde polymers, poly(methyl methacrylate), polyoxymethylene, poly(p-phenylene), poly-p-phenylene sulphide, poly(p-phenylene) vinylene, polypyrrole, polypropylene, polystyrene, polytetrafluoroethylene, polythiophene, polyurethane or amino, polyvinyl chloride, polyvinyl alcohol, polyvinylidene fluoride, ethylene propylene copolymer, urea-formaldehyde polymers, urethane polyester or urethane polyether, and any of their possible combinations in liquid form;
according to the present invention "in liquid form", means that at room temperature it is spontaneously in liquid form; in the case where a polymer is used which at room temperature is not in liquid form, it must be dissolved/solubilized/liquefied by the use of a suitable solvent or by the use of heat, i.e. bringing it to its melting temperature;
wherein:
if said polymer in liquid form is a conductive polymer, it will be used as such, i.e. without further integration (with a conductive metallic or non-metallic material) and the process will continue going directly to the third step;
if said polymer in liquid form is a non-conductive or poorly conductive polymer, it must be subjected to the second step treatment.

Second Step:
at least one metallic and/or non-metallic electrical conductive material is added to the non-conductive polymer of the first step; in which said polymer is selected from the group comprising: carbon; carbon nanotubes; carbon nanohorns; carbon black; graphene, carbon fullerenes; silver; copper; gold; aluminium; zinc; chromium; tin; iridium; tungsten; nickel; iron; platinum; lead; Indium-tin oxide (ITO); aluminium-tin oxide (AZO); at a dose ranging from 0% to 40%; preferred is a dose ranging from 0.01-35%; particularly preferred is a dose of 1-30%;
wherein:
carbon is in the form of carbon fibre, carbon nanofibers, carbon nanotubes, carbon black or carbon nanoclays, carbon nanohorns;
graphene is in the form of graphene, graphene oxide, graphene nanoplatelets or fullerene;
the metal is in the form of powder, dispersion, gel, particles, microparticles or nanoparticles and/or nanowires;
conductive ceramics such as indium-tin oxide (ITO) or aluminium tin oxide (AZO), are in the form of powder, dispersion, gel, particles, microparticles or nanoparticles and/or nanowires;
it is evident to the skilled in the art that the dose/amount of electrical conductive material to be added to the polymer will depend on the conductive characteristics of the polymeric material used and the degree of conductivity to be achieved. Said degree of conductivity to be achieved will be easily determined by a skilled in the art; and the combination/mixture/suspension thus obtained is kept under stirring for a period of few minutes until few hours;

Third Step:

the liquid mass coming from the first or the second step, kept under stirring, is poured into a screw extruder, brought to moulding temperature and moulded into a suitable mould.

After cooling, the semi-finished product thus obtained is mechanically machined to obtain an electrode having the desired shape and dimensions and ready to be connected to the electronic measuring device (thermoplastic polymers).

Alternatively, the liquid mass of the first or second step, maintained under stirring, is poured into a mould and allowed to cool and optionally to cure.

The semi-finished product thus obtained is mechanically processed obtaining a product having the desired electrode shape and size, ready to be connected to the electronic measuring device (thermosetting polymers).

The three-step preparation method described above can be described in a different way, while maintaining all its essential characteristics.

It is therefore a further object of the present invention a method for the preparation of a polymeric matrix electrode in which:

to a polymer in liquid form selected from the group above mentioned in the first step at least one metallic and/or non-metallic electrical conductive material selected in the group above mentioned in the second step is added at a dose ranging from 0% to 40%; preferred dose ranging from 0.01-35%; particularly preferred is a dose of 1-30%; the mixture thus obtained is kept under stirring for a period of a few minutes up to a few hours and then poured into a screw extruder, brought to moulding temperature and moulded into an electrode-shaped mould;

or:

poured into a mould and allowed to cool and optionally to cure;

after cooling, the semi-finished product thus obtained is mechanically processed obtaining an electrode having the desired shape and dimensions and ready to be connected to the electronic measuring device.

By the term "cure" or "to cure" according to the present invention, it is meant the transformation following cross-linking reactions (process by which the polymer chains undergo a reaction which creates bonds between different chains at the level of reactive functional groups), which occurs between the polymer chains with strong bond formation (covalent or ionic) (IUPAC, Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006—) created by M. Nic, J. Jirat, B. Kosata; updates compiled by A. Jenkins. ISBN 0-9678550-9-8. https://doi.org/10.1351/goldbook).

In the first step, second step, third step, in the molding or in the cooling and/or curing step in the mould, one or more excipients, diluents, dyes, hardeners, rubbers, elasticizing agents, oils, metal salts, and/or fluidizing agents can be optionally added; and one or more thermal treatments; Industrially acceptable, such as those described in "Composites manufacturing: materials, product, and process engineering" di Mazumdar, Sanjay K ISBN 0-8493-0585-3 2002 CRC-press".

A further object of the present invention is an electrode prepared using the polymeric matrix obtained with the method described above.

Another object of the present invention is an electrochemical sensor comprising at least one electrode prepared using the polymeric matrix obtained by the above described method; wherein said electrode is selected from the group comprising: auxiliary electrode, reference electrode and working electrode;

the use of a polymeric matrix comprising at least one silver-based conductive material is preferred for the reference electrode.

It is a further object of the present invention an electrochemical sensor comprising a data detection and transmission system provided with a battery or battery free type in which the variation of the signal detected by the data detection and transmission system is transferred through electrical data transmission wires, or preferably through a wireless system by means of systems known in the art such as, for non-limiting example the use of radio frequency identification (RFID) technology for the transfer of data to an external reader using a small antenna to maximize the efficiency of data collection and transmission.

This system is capable of working in "passive RFID" or battery free mode, receiving the energy necessary for data transfer directly from the reading system, with a limited reading distance (up to 10-15 m). In "active RFID mode, if equipped with a battery, it allows data to be stored in a chip and greater transmission distances to be reached. (Amendola, S., & Marrocco, G. (2017). IEEE Transactions on Antennas and Propagation, 65(2), 473-481) (Caccami, M. C., Hogan, M. P., Alfredsson, M., Marrocco, G., & Batchelor, J. C. (2018). IEEE Transactions on Antennas and Propagation, 66(2), 609-617).

A further object of the present invention is an electrochemical probe comprising at least one electrochemical sensor mentioned above.

A further object of the present invention is a polymeric material/compound selected from the group comprising: Tecapeek ELS CF30 Black®, Tecapeek ELS nano Black®, Tecaform AH ELS black °, Tecaflon PVDF ELS black; Tecapeek SD black °, LARAMID K/40 HM®, LARPEEK 10 K/20®, LARPEEK 10 K/30®, LARPEEK 10 K/40®, LARTON K/20®, LARTON K/30®, LARTON K/40 HM®, LARTON L K/20®, LASTILAC RT K/b®, LATAMID 66 H2 K/20®, LATAMID 66 H2 K/30®, LATAMID 66 H2 K/40®, LATAMID 66 H2 K/50®, LATER 4 K/30®, LATICONTHER 52/11 GR/70®, LATICONTHER 62 GR/50®, LATICONTHER 62 GR/50-V0®, LATICONTHER 62 GR/70®, LATICONTHER 75 GR/50®, LATICONTHER 80 GR/50®, LATICONTHER 87/28 GR/50®, LATIGRAY 82-03 CW/95®, LATIGRAY 82-03 CW/96 F3®, LATIGRAY 82-05 CX/90®, LATILUB 87/28-175T K/15®, LATIMASS 82-05 D040®, LATIOHM 57-05 PD01 G/15®, LATIOHM 62-03 PD01 G/20®, LATIOHM 66-04 PD01 G/25-V0CT1®, LATIOHM 66-07 PD08 G/30®, LATIOHM 73-09 PD01 G/20®, LATIOHM 75/4-03 PD01 G/20®, LATIOHM 75/4-08 PD01 G/30®, LATIOHM 80-04 PD01 G/30®, LATIOHM 80-05 CNT GCE/500®, LATIOHM 82-02 PD09®, LATIOHM 85-06 PD01 G/15®, LATIOHM 87/26-06 PD01-V1®, LATIOHM 87/28-05 PD01 G/10®, LATIOHM 88/10-06 CNT®, LATIOHM 90/13-09 PD01 G/10®, LATISHIELD 36/AR-08A G/17-V0E®, LATISHIELD 36/AR-10A-V0E®, LATISHIELD 36/SP-05A®, LATISHIELD 38/11-08A G/10®, LATISHIELD 52/5-07A®, LATISHIELD 66-08A G/25-V0 KB1®, LATISHIELD 66-10A®, LATISHIELD 66-10A G/15®, LATISHIELD 66-10A H2 CETG/400®, LATISHIELD 66-13A G/30®, LATISHIELD 73/13-07A®, LATISHIELD 75/4-10A®, LATISHIELD 85-08A G/20®, LATISHIELD 87/28-10A®, LATISHIELD 87/28-10A G/20®, LATISTAT 36/MR-04®, LATISTAT 45/7-02®, LATISTAT 47/7-03®, LATISTAT 48/9900-03®, LATISTAT 52/7-02®, LATISTAT 52/7-02 MI/30®, LATISTAT 62-06 K/b®, LATISTAT 66-06®, LATISTAT 83-OS® e LATISTAT 87/28-06®; for use in the preparation of an electrode selected from the group comprising: counter electrode, reference electrode and working electrode.

A further object of the present invention is a kit comprising at least one probe and at least one electrode according to the invention, at least one electronic control and/or actuation unit, at least a display optionally touchscreen, and at least one measurement channel for storing the detected electrochemical parameters; and at least one data transmission system provided with a battery or battery-free type.

The possibility of making electrodes with conductive polymers allows to obtain the thermal, electrical and/or electrochemical properties of the metal electrodes, associated with a simpler processability of the polymer. In this way it is possible to make electrodes with desired geometry and material, without having to fall within the technological limits of the conventional mechanical workings. In this way it is possible to realize the electrodes directly on the support reducing both the problems of hydraulic sealing and the quantity of noble metal necessary for the purpose.

Using the smaller amount of noble metal to make the electrodes produces a reduction in costs; using the desired electrode geometry allows to increase the performance of the probes.

A fundamental role in the measurement chain covers the electrical connection between the metal of the electrodes and the electrical wire with which the signal is transferred to the measuring device. This connection is generally achieved by means of a brazing, which consists in indirectly joining the pieces by melting between the adjacent and heated parts a material provided with a melting point at a lower temperature, which in practice performs the function of "glue" between the two pieces.

This brazing, in addition to being a very delicate point, can trigger undesired electrochemical reactions if it comes into contact with the liquid, compromising the operation of the probe.

Thanks to the use of the polymer matrix according to the invention it is now possible to integrate the electrical connection directly into the polymeric material of which the auxiliary, reference and/or working electrode is composed, or to use the polymer itself as adhesive between the electrode and the wire connecting to the instrument.

The following Examples illustrate the invention without limiting it and by referring to the Figures described above.

DETAILED DESCRIPTION OF THE INVENTION

Examples

Example 1

Method of Preparation of an Electrode by Using Polyvinylidene Fluoride (PVDF) (Thermoplastic) in Combination with Carbon Black 610 mg of CB in 60 ml of DMF (N,N-dimethylformamide) were dispersed, the resulting suspension was sonicated (30% amplitude with a power of 200 W) in ice bath for at least one hour.

5 g of PVDF pellets to the dispersion of sonicated CB were added.

The solution thus obtained was placed under gentle stirring for two hours at 90° C. and subsequently at 60° C. until evaporation of the solvent.

The solid thus obtained was collected and cut into pellet form.

The pellet was placed in a screw extruder and brought to the moulding temperature of about 175° C., to be moulded in the desired shape.

The semi-finished product thus obtained was mechanically refined to obtain an electrode having the desired shape and size, ready to be connected to the electronic measuring device.

Example 2

Method of Preparation of an Electrode, by Using Polyvinylidene Fluoride (PVDF) in Combination with Carbon Nanotubes Following the method described in Example 1, using 122 mg of carbon nanotubes, an electrode having the desired shape and size, ready to be connected to the electronic measuring device was obtained.

Example 3

Method of Preparation of an Electrode Based on PET (Thermoplastic) Polyethylene Terephthalate in Combination with Carbon Nanotubes Following the method of Example 2, but replacing PVDF with PET (polyethylene terephthalate), an electrode having desired shape and size, ready to be connected to the electronic measuring device was obtained.

Example 4

Method of Preparation of an Electrode, by Using an Epoxy Resin (Thermosetting) in Combination with Carbon Nanofibers 498 mg of carbon nanofibers were dispersed in 50 ml of diethylene glycol butyl ether (BGE) and sonicated for one hour in an ice bath (with a 30% amplitude and 200 W power). 10 g of epoxy resin (DGEBA Araldite LY554®) in the dispersion of BGE and carbon nanofibers were added.

The compound thus obtained was kept under stirring at room temperature until complete evaporation of the BGE solvent.

in a dispersion of resin and carbon nanofibers, 6 g of hardener (Araldite HY956® triethyleneamines) were added; the resulting compound so obtained was subjected to gentle mechanical stirring for 5 minutes, and then poured into an electrode-shaped mold.

After 24 hours at room temperature the final shape of the electrode, ready to be connected to the electrical measuring system, was obtained.

Example 5

Method of Preparation of an Electrode, by Using an Epoxy Resin (Thermosetting) in Combination with Carbon Nanofibers Following the method of Example 4, the BGE solvent was removed mechanically by filtering the dispersion of carbon nanofibers and BGE.

The carbon nanofibers, disentangled by sonication were collected on the filter paper and allowed to dry. After drying the fibres were dispersed in the resin by mechanical stirring.

Example 6

Method of Preparation of an Electrode by Using an Epoxy Resin (Thermosetting) in Combination with Carbon Nanofibers Following the method of Example 5, the carbon nanofibers were dispersed in the hardener instead of the resin, dispersed by mechanical stirring and then added to the resin.

Example 7

Method of Preparation of an Electrode by Using an Epoxy Resin (Thermosetting) in Combination with Carbon Nanotubes Following the method of Example 4, the carbon nanofiber was replaced with an equal amount of carbon nanotubes.

Example 8

Method of Preparation of an Electrode by Using an Epoxy Resin (Thermosetting) in Combination with Carbon Nanotubes Following the method of Example 5, the carbon nanofiber was replaced with an equal amount of carbon nanotubes.

Example 9

Method of Preparation of an Electrode, by Using an Epoxy Resin (Thermosetting) in Combination with Carbon Nanotubes Following the method of Example 6, the carbon nanofiber was replaced with an equal amount of carbon nanotubes.

Example 10

Method of Preparation of an Electrode by Using an Epoxy Resin (Thermosetting) in Combination with Silver Nanopowder Following the method of Example 4, the carbon nanofiber was replaced with an equal amount of silver nanopowder.

Example 11

Method of Preparation of an Electrode by Using an Epoxy Resin (Thermosetting) in Combination with Silver Nanopowder Following the procedure of Example 5, the carbon nanofiber was replaced with an equal amount of silver nanopowder.

Example 12

Method of Preparation of an Electrode, by Using an Epoxy Resin (Thermosetting) in Combination with Silver Nanopowder Following the method of Example 6, the carbon nanofiber was replaced with an equal amount of silver nanopowder.

Example 13

Method of Preparation of an Electrode, by Using an Epoxy Resin (Thermosetting) in Combination with Gold Nanoparticles Following the method of Example 4, the carbon nanofiber was replaced with an equal amount of gold nanoparticles.

Example 14

Method of Preparation of an Electrode, by Using an Epoxy Resin (Thermosetting) in Combination with Gold Nanoparticles Following the method of Example 5, the carbon nanofiber was replaced with an equal amount of gold nanoparticles.

Example 15

Method of Preparation of an Electrode, by Using an Epoxy Resin (Thermosetting) in Combination with Gold Nanoparticles Following the method of Example 6, the carbon nanofiber was replaced with an equal amount of gold nanoparticles.

Example 16

Method of Preparation of an Electrode, by Using an Epoxy Resin (Thermosetting) in Combination with Platinum Nanoparticles Following the method of Example 4, the carbon nanofiber was replaced with an equal amount of platinum nanoparticles.

Example 17

Method of Preparation of an Electrode, by Using an Epoxy Resin (Thermosetting) in Combination with Platinum Nanoparticles Following the method of Example 5, the carbon nanofiber was replaced with an equal amount of platinum nanoparticles.

Example 18

Method of Preparation of an Electrode, Using an Epoxy Resin (Thermosetting) in Combination with Platinum Nanoparticles Following the method of Example 6, the carbon nanofiber was replaced with an equal amount of platinum nanoparticles.

Example 19

Figure 1:
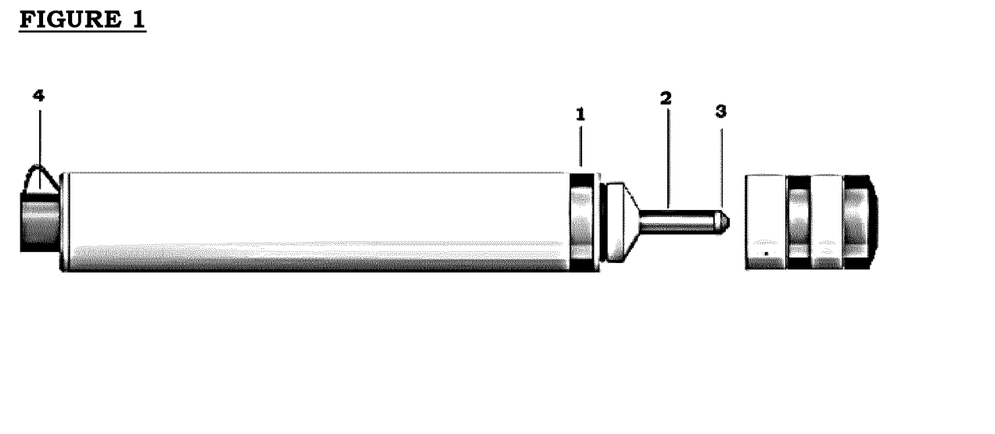
In FIG. 1, the electrochemical probe according to the present invention is shown in which:
number 1 indicates the counter electrode made of a "polymer matrix",
number 2 indicates the reference electrode made of a "polymer matrix",
number 3 indicates the working electrode made of a "polymer matrix", and number 4 indicates the electrical connection zone.
Figure 2:
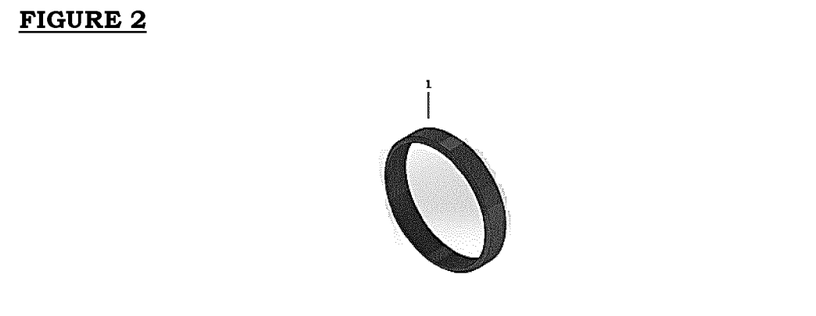
FIG. 2 shows an example of a "polymer matrix" counter electrode.
Figure 3:
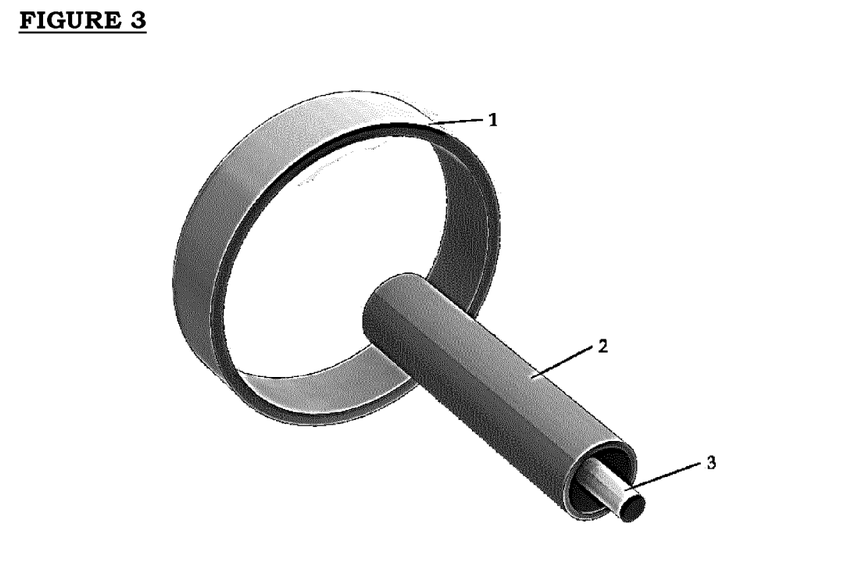
In FIG. 3 are shown, in more detail manner, the three electrodes, made of a "polymer matrix" according the present invention, in which:
number 1 indicates the counter electrode,
number 2 indicates the reference electrode, and
number 3 indicates the working electrode.

Method of Preparation of a Counter Electrode, by Using a Polyetherketone in Combination with Carbon Nanotubes A polyetherketone bar supplemented/combined with carbon nanotubes (TECAPEEK ELS nano Black®), having a surface resistivity of $10^2$-$10^4 \Omega$ and a Volume Resistivity $10^3$-$10^5$ $\Omega$/cm, was subjected to turning and cutting until a ring of internal diameter of 23 mm and external diameter of 25 mm was obtained (see FIG. 2). The ring was housed on the probe seat and the wire necessary for electrical connection was inserted into a suitable groove. The electrical contact and the hydraulic seal were ensured by a two-component, electrically conductive epoxy resin-based adhesive filled with carbon black nanoparticles.

Example 20

Method of Preparation of a Counter Electrode by Using a Polyetherketone in Combination with Carbon Fibres Following the procedure of Example 19, TECAPEEK ELS nano Black® was replaced with TEKAPEEK ELS CF30 Black®.

Example 21

Measurement of Free Chlorine, by Using an Electrochemical Probe in which the Counter Electrode was Obtained Following the Method of Example 19

The term free chlorine refers to the sum of the hypochlorous acid and the hypochlorite ions which are formed by adding, in aqueous solution,
substances such as:
sodium hypochlorite;
calcium hypochlorite;
gaseous chlorine;
isocyanuric acid derivatives (dichloro and trichloro).

Two electrochemical probes were used for the measurement of free chlorine, in which:
the first probe used was a probe known in the art (free chlorine probe, organic and inorganic; Tecnosens s.r.l. model NCL T20 e NCL T2 available in http://www.t-sens.eu) wherein the working electrode is in gold, the reference electrode is in silver, and the counter electrode in steel;
the second probe used was the probe known in the art in which the steel counter electrode was replaced with a polymeric matrix counter electrode obtained using the method described in Example 19 according to the present invention.

The measurement was carried out by inserting the probes into a hydraulic circuit in which the free chlorine content present in the water was varied.

Figure 4:
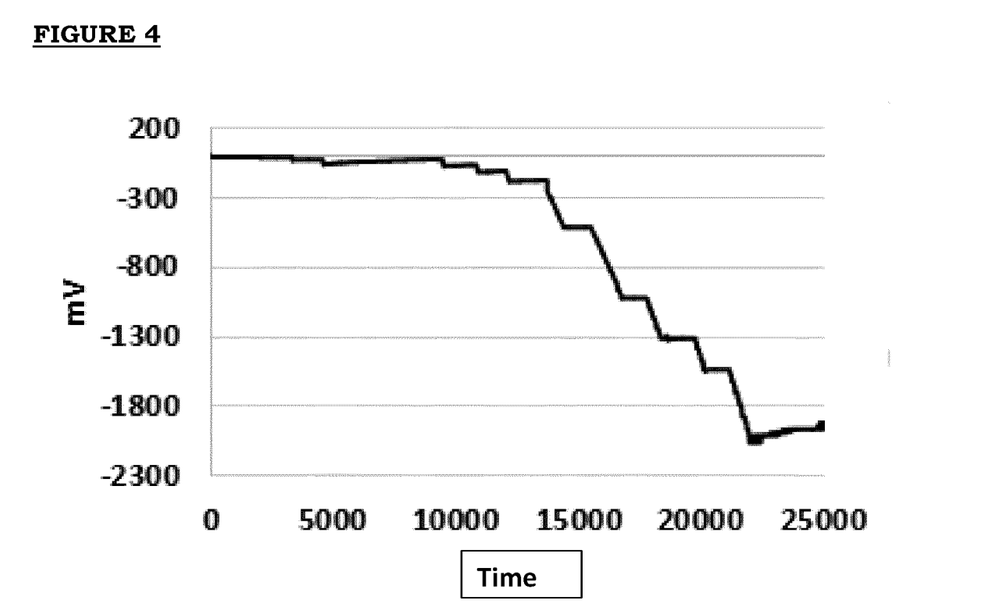
FIG. 4 shows the trend over time of the measurement system signal output, varying the free chlorine concentration in the analysed water: 0.15, 0.30, 0.40, 0.80, 1.20, 1.90, 1.40, 5.0, 9.5, 13.0, 15.0, 18.0 ppm, relative to a probe known to the art.
Figure 5:
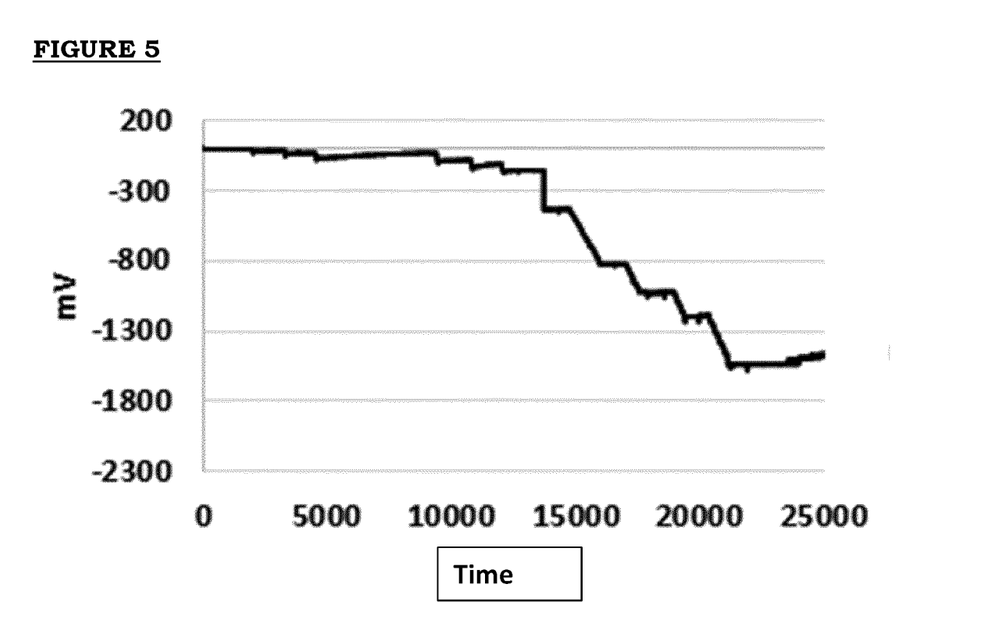
FIG. 5 shows the trend over time of the variation of the measurement system output signal using a probe known in the art wherein the counter electrode was prepared using a compound according to the present invention (PEEK modified with carbon nanotubes, see Example 19);
while the reference electrodes and working electrodes were those known in the art; the concentration of free chlorine in the water analyzed was: 0.15, 0.30, 0.40, 0.80, 1.20, 1.90, 1.40, 5.0, 9.5, 13.0, 15.0, 18.0 ppm.

The results obtained with the probe known to the art are shown in FIG. 4 while the results obtained with the probe according to the present invention are shown in FIG. 5.

The images show the variation in time of the measurement system signal output as the concentration of free chlorine in the analysed water varies.

It is known to the skilled in the art that the variation of the signal is due to a reduction reaction.

The pH value at which the tests were carried out was between 4 and 10; the temperature value remained between 0° C. and 45° C.

The results obtained shows that by carrying out the measurements with the probe with the polymeric matrix electrode according to the invention in:
a measurement range comprised between 0.010 and 2.000 ppm and between 0.05 and 20 ppm;
a pH range of the water analysed: 4-10 (to the skilled in the art the dependence of the sensitivity on variation of the pH is known);
with a signal slope varying between ±50% with respect to the nominal slope;
with a temperature range: between 0 and 45° C.;
measurements/values similar to those obtained with the probe of the art with a steel counter-electrode were obtained.

In this experimental model increasing the concentration of dissolved salts in water, different behaviours were observed between the prior art probe (steel counter electrode) and the probe in which the counter electrode was in a polymeric matrix according to the invention.

In fact, when the value of 10,000 ppm of salts dissolved in water were exceeded, corrosion products were formed on the steel count electrode made the probe steel electrode unusable; while the probe with a polymeric matrix counter electrode according to the invention showed no corrosion product, it was then usable for further measurements of free chlorine.

After one month of measurements, in the presence of a salt concentration in water greater than 10,000 ppm, the counter electrode according to the invention continued to show no sign of corrosion.

Example 22

Measurement of Free Chlorine Using an Electrochemical Probe Comprising the Counter Electrode Obtained as Described in Example 20 According to the Invention Following the method described in Example 21, two electrochemical probes for the measurement of free chlorine were used, in which:
the first probe used was a probe known in the art (free chlorine probe, organic and inorganic; Tecnosens s.r.l. model NCL T20 e NCL T2 available in http://www.t-sens.eu) where the working electrode is in gold, the reference electrode is in silver, and the counter electrode is in steel;
the second probe used was the probe known in the art, in which the steel counter electrode was replaced with a polymeric matrix counter electrode according to the present invention, obtained using the method described in Example 20.

Figure 6:
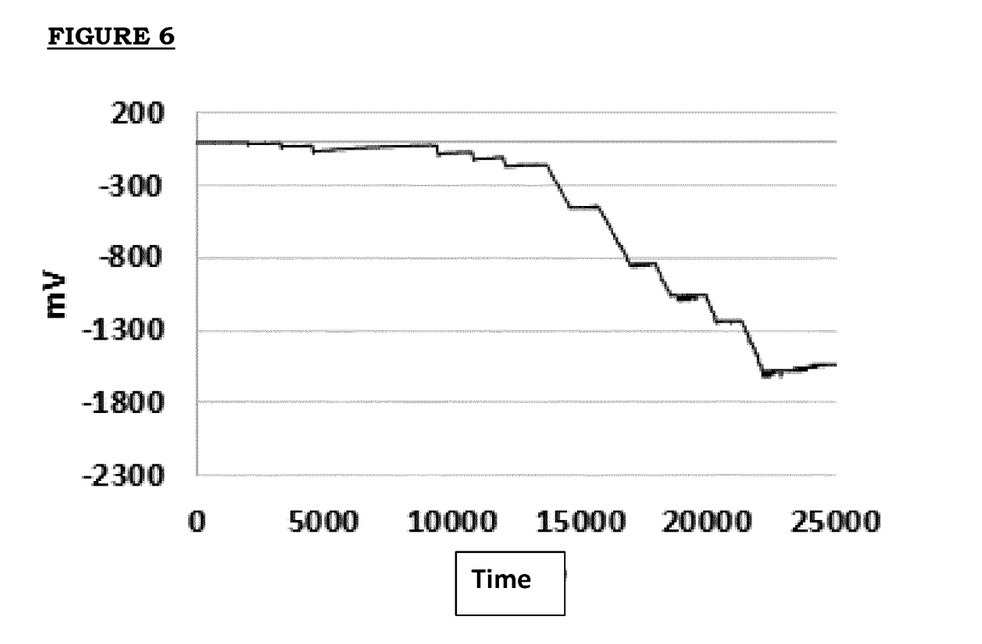
FIG. 6 shows the trend over time of the variation of the measurement system output signal by using a probe known in the art wherein the counter electrode was prepared using a compound according to the present invention (carbon fibres filled PEEK, see Example 20); while the reference and working electrodes were those known in the art; the concentration of free chlorine in the analysed water was: 0.15, 0.30, 0.40, 0.80, 1.20, 1.90, 1.40, 5.0, 9.5, 13.0, 15.0, 18.0 ppm.

The results obtained were similar to those reported in Example 21 and are shown in FIG. 6.

FIG. 6 shows the variation in time of the measurement system signal output as the free chlorine concentration in the analysed water varies.

Also in this case, the polymeric matrix counter electrode according to the invention showed corrosion resistance as in Example 21.

Example 23

Measurement of Free Chlorine Using the New Reference Electrode in Polymer Matrix Obtained as Described in Example 11

For the measurement of free chlorine, following the method described in the previous Examples, a reference electrode in a silver polymeric matrix, obtained as described in Example 11, was used.

The results obtained were comparable to those reported in Examples 21-22.

As stated above, the reference electrode (including that of the present invention) is immersed in an electrolytic solution, which protects and allows its function.

The advantage in the use of the reference electrode according to the present invention, in substitution of the silver electrode present in the probes known in the art, is linked both to the significant reduction of the costs of the raw material and of the industrial method for preparing the electrode.

Example 23

Measurement of Free Chlorine Using the New Working Electrode of Example 14

The gold working electrode of the prior art probe was replaced with the working electrode obtained as described in Example 14 and used for the measurement of free chlorine following the method described in Example 21.

The results obtained were comparable to those reported in Examples 21-22.

As stated above, the working electrode (including that of the present invention) is immersed in an electrolytic solution, which protects and allows its function.

The advantage in the use of the working electrode according to the present invention, instead of the gold electrode present in the probes known in the art, is linked both to the significant reduction of the costs of the raw material and of the industrial method for preparing the electrode.

Example 24

Measurement of Free Chlorine Using the Counter Electrode of Example 19 and the Reference Electrode of Example 11.

The counter electrode and the reference electrode of the prior art probe were replaced with the counter electrode of Example 19 and the reference electrode of Example 11, and used for the measurement of free chlorine following the method described in Example 21.

The results obtained were comparable to those reported in Example 21-23.

The polymeric matrix counter electrode according to the invention showed corrosion resistance such as that of Example 21.

Moreover, the advantage in the use of the reference electrode according to the present invention, instead of the silver electrode present in the probes known in the art, is linked both to the significant reduction of the costs of the raw material and of the industrial method for preparing the electrode.

Example 25

Measurement of Free Chlorine Using the New Counter Electrode of Example 19 and the New Working Electrode of Example 14

The counter electrode and the working electrode of the prior art probe were replaced with the counter electrode of Example 19 and the working electrode of Example 14, and used for the measurement of free chlorine following the method described in Example 21.

The results obtained were comparable to those reported in Examples 21-24.

Also in this case, the polymeric matrix counter electrode according to the invention showed corrosion resistance as in Example 21.

Moreover, the advantage in the use of the working electrode according to the present invention, instead of the gold electrode present in the probes known in the art, is linked both to the significant reduction of the costs of the raw material and of the industrial method for preparing the electrode.

Example 26

Measurement of Free Chlorine Using the New Reference Electrode of Examples 11 and the New Working Electrode of Example 14

For the measurement of free chlorine, following the method described in Example 21, the reference electrode of Example 11 and the working electrode of Example 14, in place of the silver reference electrode and the gold working electrode of the prior art probe were used.

The results obtained were comparable to those reported in Examples 21-25.

Also in this case the use of the reference electrode and the working electrode according to the present invention, in place of the silver and gold electrode, respectively, present in the probes known in the art, is linked both to the significant reduction of the costs of the raw material and of the industrial method for preparing the electrode.

Example 27

Measurement of Free Chlorine Using the New Reference Electrode of Example 11, the New Working Electrode of Example 14 and the New Counter Electrode of Example 19

For the measurement of free chlorine, following the method described in Example 21, the reference electrode of Example 11, the working electrode of Example 14, and the counter electrode of Example 19, instead of the silver reference electrode, the gold working electrode and the steel counter electrode of the prior art probe were used.

The results obtained were comparable to those reported in Examples 21-26.

Also in this case the use of the reference electrode and the working electrode according to the present invention, in place of the silver and gold electrode, respectively, present in the probes known in the art, is linked both to the significant reduction of the costs of the raw material and of the industrial method for preparing the electrode.

Example 28

Measurement of Free Chlorine Using the New Counter Electrode of Example 10; the Reference Electrode of Example 11, and the Working Electrode of Example 1

For the measurement of free chlorine, following the method described in Example 21, the counter electrode of Example 10; the reference electrode of Example 11; and the working electrode of Example 1 in place of the electrodes in the probe known to the art, was used.

The results and advantages obtained were comparable to those reported in Examples 25-27.

Example 29

Measurement of Free Chlorine Using the New Counter Electrode of Example 1; the Reference Electrode of Example 11, and the Working Electrode of Example 10.

For the measurement of free chlorine, following the method described in Example 21, the counter electrode of Example 1; the reference electrode of Example 11; and the working electrode of Example 10 instead of the electrodes in the probe known to the art, were used.

The results and advantages obtained were comparable to those reported in Examples 25-27.

The invention claimed is:

1. A method for preparing a polymeric matrix electrode comprising:
    adding to a polymeric matrix in liquid form a metallic and/or non-metallic electrical conductive material to obtain a mixture, wherein
    the polymeric matrix is selected from the group consisting of: acrylonitrile-butadiene-styrene copolymer, ethylene-vinyl acetate, polyacetal, polyamide 6, polyamide 12, polyamide 66, polyamide, polybutylene terephthalate, polycarbonate, polyetherketone, polyetheretherketone, polyether sulphone, polyethylene, low-density polyethylene, high-density polyethylene, polyphenylene sulfide, poly(phenylene oxide), polyoxymethylene, polypropylene, polyvinylidene fluoride, and any of their combinations;
    the metallic and/or non-metallic electrical conductive material is selected from the group consisting of: carbon; carbon nanotubes; carbon nano-horn; carbon black; graphene; fullerene; silver; copper; gold; aluminum; zinc; chromium; tin; iridium; tungsten; nickel; iron; platinum; lead; aluminum-tin oxide (AZO); and indium-tin oxide (ITO); and conductive ceramics; wherein said metallic and/or non-metallic electrical conductive material added at a dose 0.1-40% to the polymeric matrix; wherein:
    the carbon is in the form of carbon fiber, carbon nano-fiber, carbon nanotubes, carbon black, carbon nano-clays or carbon nano-horn,
    the graphene is in the form of graphene oxide, graphene, nano platelets or fullerene,
    the metallic electric conductive material is in the form of powder, dispersion, gel, particles, microparticles or nanoparticles and/or nanowire,
    the conductive ceramics are in the form of powder, dispersion, gel, particles, microparticles or nanoparticles and/or nanowire;
    maintaining the mixture so obtained under stirring, for a time period of 1-120 minutes, and
    putting the stirred mixture into a mold, and after molding, a polymeric matrix electrode is prepared by machining.

2. The method according to claim 1, wherein the metallic and/or non-metallic electrical conductive material is added at a dose between 0.1-35% to the polymeric matrix.

3. The method according to claim 1, wherein the metallic and/or non-metallic electrical conductive material is added at a dose between 1-30% to the polymeric matrix.

* * * * *